(12) United States Patent
Wang et al.

(10) Patent No.: US 9,119,549 B2
(45) Date of Patent: Sep. 1, 2015

(54) METHOD FOR DEVELOPING TEST FOR NEUROPSYCHIATRIC DISEASE

(75) Inventors: Lu-yong Wang, Plainsboro, NJ (US); Xiaoguang Lu, Plainsboro, NJ (US); Bogdan Georgescu, Plainsboro, NJ (US); Daniel Fasulo, Titusville, NJ (US)

(73) Assignee: Siemens Aktiengesellschaft, Munich (DE)

( * ) Notice: Subject to any disclaimer, the term of this patent is extended or adjusted under 35 U.S.C. 154(b) by 1904 days.

(21) Appl. No.: 12/264,361

(22) Filed: Nov. 4, 2008

(65) Prior Publication Data

US 2009/0124886 A1 May 14, 2009

Related U.S. Application Data

(60) Provisional application No. 60/987,212, filed on Nov. 12, 2007.

(51) Int. Cl.
*A61B 5/05* (2006.01)
*A61B 5/055* (2006.01)
*A61B 5/00* (2006.01)

(52) U.S. Cl.
CPC .............. *A61B 5/055* (2013.01); *A61B 5/7267* (2013.01)

(58) Field of Classification Search
USPC ........................................................ 600/410
See application file for complete search history.

(56) References Cited

U.S. PATENT DOCUMENTS

| 2003/0229278 | A1* | 12/2003 | Sinha ............................ 600/407 |
| 2004/0096089 | A1* | 5/2004 | Borsook et al. ............... 382/131 |
| 2005/0215884 | A1* | 9/2005 | Greicius et al. ............... 600/410 |
| 2006/0104494 | A1* | 5/2006 | Collins et al. ................. 382/128 |
| 2006/0120584 | A1* | 6/2006 | Hillman ........................ 382/128 |

OTHER PUBLICATIONS

Alzheimer Disease: Evaluation of a Functional MR Imaging Index as a Marker by Li et al.(Oct. 2002).*
Gaussian Mean-Shift is an EM Algorithm by Carreira-Perpinan (May 2007).*
Kontos et al., "Detecting Discriminative Functional MRI Activation Patterns Using Space Filling Curve", IEEE EMBC 2003, pp. 963-966.*

* cited by examiner

*Primary Examiner* — Long V Le
*Assistant Examiner* — Bradley Impink

(57) ABSTRACT

A method for generating classifiers for identifying neuropsychiatric disease includes acquiring functional neuroimaging data. The acquired functional neuroimaging data may be registered to an atlas of the brain. A discriminative mask is generated based on the registered functional neuroimaging data and the generated discriminative mask is applied to the registered functional neuroimaging data. One or more classifiers are generated for identifying neuropsychiatric disease based on the masked functional neuroimaging data. The accuracy of the generated classifiers may be verified. The generated classifiers may then be used to identify neuropsychiatric disease.

6 Claims, 3 Drawing Sheets

METHOD FOR DEVELOPING TEST FOR NEUROPSYCHIATRIC DISEASE

CROSS-REFERENCE TO RELATED APPLICATION

The present application is based on provisional application Ser. No. 60/987,212, filed Nov. 12, 2007, the entire contents of which are herein incorporated by reference.

BACKGROUND OF THE INVENTION

1. Technical Field

The present disclosure relates to neuropsychiatric disease and, more specifically, to a method for developing a test for neuropsychiatric disease.

2. Discussion of Related Art

Autism is a neuropsychiatric disease and brain development disorder that affects a large number of people. Autism is characterized by impaired social interaction, problems with verbal and nonverbal communication, and unusual, repetitive or severely limited activities and interests. It is estimated that three to six children out of every 1,000 will have autism. Males are four times as likely to have autism as females.

Previous research pertaining to structural magnetic resonance imaging (MRI) has been performed to identify volumetric differences and elucidate the neuro-developmental underpinnings and brain behavior relationship in autism. Based on this and other research, it is believed that there may be a strong connection between autism and abnormal brain activity.

Functional magnetic resonance imaging (fMRI) is a recently developed form of neuroimaging that may be used to aid in the understanding of activity above and beyond what is possible by ordinary structural MRI. Functional Magnetic resonance imaging measures the hemo-dynamic response related to neural activity in the brain or spinal cord of humans or animal subjects. Using fMRI, brain diseases may be diagnosed and analyzed by detecting the brain activation pattern changes between patients with known cases of the disease in question and a control group of patients that are known to be free of the disease in question.

This may be accomplished, for example, by monitoring the hemo-dynamic response of the subject while exposed to a particular stimulus that is known or believed to illicit distinct responses in subjects that have a particular disease and subjects that do not have the particular disease.

However, while fMRI has been successfully applied to the diagnosis and analysis of some neuropsychiatric disease, other neuropsychiatric diseases, such as autism, have proven very difficult to characterize based on measured hemo-dynamic response levels. This is in part due to a vague and/or noisy activation signals that are generally observed during fMRI analysis.

For this and other reasons, progress in developing tests for neuropsychiatric diseases using functional neuroimaging such as fMRIs has proven especially difficult. Without adequate methods for developing tests for neuropsychiatric diseases, research pertaining to diseases such as autism may progress more slowly than is desired. Accordingly, advances in the development of tests for neuropsychiatric diseases may facilitate research, increase understanding and help to bring about a treatment or cure to neuropsychiatric diseases such as autism.

SUMMARY

A method for generating classifiers for identifying neuropsychiatric disease includes acquiring functional neuroimaging data; registering the acquired functional neuroimaging data to an atlas of the brain; generating a discriminative mask based on the registered functional neuroimaging data; applying the generated discriminative mask to the registered functional neuroimaging data; and generating one or more classifiers for identifying neuropsychiatric disease based on the masked functional neuroimaging data.

The acquiring functional neuroimaging data may include functional neuroimaging data of patients known to have the neuropsychiatric disease and patients known not to have the neuropsychiatric disease. The functional neuroimaging data may be fMRI data acquired using an MR imager.

Prior to registering the acquired functional neuroimaging data to an atlas of the brain, the acquired functional neuroimaging data may be pre-processed to place the acquired functional neuroimaging data into a scale and orientation that matches the atlas of the brain. Alternatively, or additionally, prior to registering the acquired functional neuroimaging data to an atlas of the brain, the acquired functional neuroimaging data may be pre-processed to correct for patient motion during the acquiring functional neuroimaging data.

Generating the discriminative mask based on the registered functional neuroimaging data may include examining a correlation of brain activity for each region of the brain with respect to functional neuroimaging data from an experimental group and functional neuroimaging data from a control group. The experimental group may include patients known to have the neuropsychiatric disease and the control group may include patients known not to have the neuropsychiatric disease.

The discriminative mask may contain voxels that demonstrate a difference between the activity of the control group and the experimental group. Those regions that do not show a difference in activity between the groups may be omitted from the discriminative mask.

Activation region clustering and filtering may be performed on the masked functional neuroimaging data prior to generating the classifiers to emphasize clusters of brain activity over isolated activity associated with noise or brain function that is not of diagnostic value. The activation region clustering and filtering may include performing mean shifting to identify and emphasize clusters of activity.

Generating one or more classifiers for identifying neuropsychiatric disease may include performing Principal Component Analysis (PCA) to generate the classifiers. Alternatively, or additionally, generating one or more classifiers for identifying neuropsychiatric disease may include performing Linear Descriptive Analysis (LDA) to generate the classifiers.

The method may additionally include the step of verifying whether the generated classifiers are effective. Leave one out cross validation (LOOCV) and/or receiver operating characteristic (ROC) curves may be used to verify whether the generated classifiers are effective.

A method for identifying neuropsychiatric disease includes acquiring functional neuroimaging data of a patient and applying a classifier for identifying the neuropsychiatric disease to the acquired functional neuroimaging data to determine whether the patient has the neuropsychiatric disease. The classifier is generated by acquiring functional neuroimaging training data of patients known to have the neuropsychiatric disease and patients known not to have the neuropsychiatric disease; registering the acquired functional neuroimaging training data to an atlas of the brain; generating a discriminative mask based on the registered functional neuroimaging training data; applying the generated discriminative mask to the registered functional neuroimaging training data; and generating the classifier for identifying neuropsychiatric disease based on the masked functional neuroimaging training data.

Prior to registering the acquired functional neuroimaging training data to an atlas of the brain, the acquired functional neuroimaging training data may be pre-processed to place the acquired functional neuroimaging data into a scale and orientation that matches the atlas of the brain and to correct for patient motion during the acquiring functional neuroimaging training data.

Generating the discriminative mask based on the registered functional neuroimaging training data may include examining a correlation of brain activity for each region of the brain with respect to functional neuroimaging training data from the patients known to have the neuropsychiatric disease (a experimental group) and functional neuroimaging data from the patients known to nor have the neuropsychiatric disease (a control group).

The discriminative mask may contain voxels that demonstrate a difference between the activity of the control group and the experimental group. Those regions that do not show a difference in activity between the groups may be omitted from the discriminative mask.

Activation region clustering and filtering may be performed on the masked functional neuroimaging training data prior to generating the classifiers to emphasize clusters of brain activity over isolated activity associated with noise or brain function that is not of diagnostic value. The activation region clustering and filtering may include performing mean shifting to identify and emphasize clusters of activity.

Generating one or more classifiers for identifying neuropsychiatric disease may include performing Principal Component Analysis (PCA) and/or performing Linear Descriptive Analysis (LDA) to generate the classifiers.

A computer system includes a processor and a program storage device readable by the computer system, embodying a program of instructions executable by the processor to perform method steps for identifying a region of the brain involved with a neuropsychiatric disease. The method includes acquiring functional neuroimaging data; registering the acquired functional neuroimaging data to an atlas of the brain; generating a discriminative mask based on the registered functional neuroimaging data; applying the generated discriminative mask to the registered functional neuroimaging data; and identifying a region of the brain involved with a neuropsychiatric disease based on the corresponding location on the atlas of the brain of activity data of the masked functional neuroimaging data.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings, wherein.

DETAILED DESCRIPTION OF THE DRAWINGS

Figure 1:
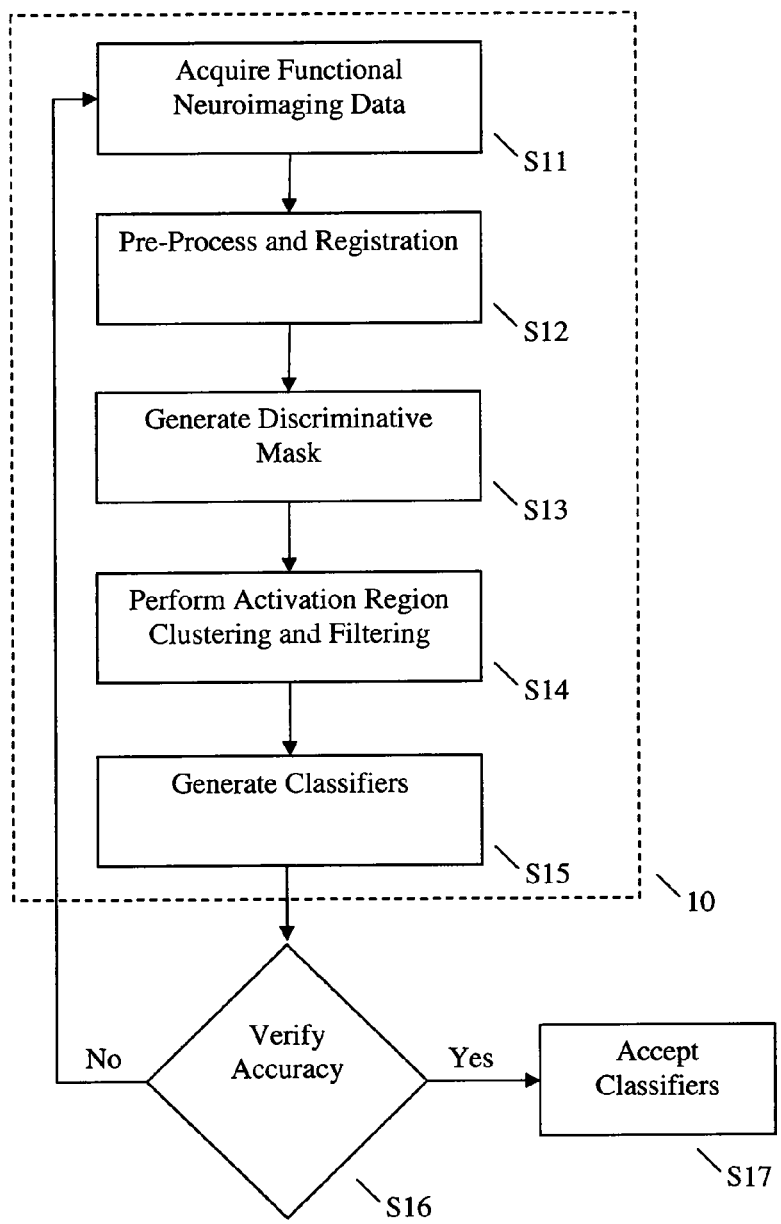
FIG. 1 is a flow chart illustration a discovery pipeline for processing functional neuroimaging data and generating pattern classifiers for identifying neuropsychiatric disease according to an exemplary embodiment of the present invention.

In describing exemplary embodiments of the present disclosure illustrated in the drawings, specific terminology is employed for sake of clarity. However, the present disclosure is not intended to be limited to the specific terminology so selected, and it is to be understood that each specific element includes all technical equivalents which operate in a similar manner.

Exemplary embodiments of the present invention seek to provide a method for developing a test for neuropsychiatric disease so that effective diagnosis of the disease may be rendered more accurately and at an earlier age. Moreover, exemplary embodiments of the present invention seek to provide an approach for determining which structures of the brain may be involved in neuropsychiatric disease so that additional scientific research may be directed towards structures of the brain that may be involved with the neuropsychiatric disease being studied. By these approaches, diagnosis and treatment of neuropsychiatric diseases such as autism may be aided.

Exemplary embodiments of the present invention may provide for a diagnostic framework for analyzing functional neuroimaging data such as fMRI images using a sequence of preprocessing steps, discriminative mask generation, region clustering, anatomical region-based analysis, learning-based subspace analysis and visualization of discriminative features.

After the data has been appropriately conditioned in accordance with exemplary embodiments of the present invention, it may then be assumed that regions of the brain that exhibit significant activation may be reacting to stimuli rather than exhibiting noise or reaction to other unrelated factors. These activated regions may then be effectively isolated, for example, using a mean shift-based approach. The regions so isolated may thereby show a correlation to instances of disease so that further research may be directed to studying the significance of the correlation between the disease and the isolated regions of the brain and/or examination of the activation of the isolated regions of the brain under appropriate stimulus may be used as a test for detecting instances of the disease.

FIG. 1 is a flow chart illustration an approach for processing functional neuroimaging data, for example, fMRI data, according to an exemplary embodiment of the present invention. After processing the acquired fMRI data in accordance with this approach, the data may be effectively utilized for diagnosis and/or focusing research as described above.

First, functional neuroimaging data may be acquired (Step S11). The functional neuroimaging data may be, for example, fMRI data. Then, the acquired functional neuroimaging data may be pre-processed and registered to an image or representation of the brain (Step S12) so that the activity data of the neuroimage may be understood within a proper context. By determining which structural components of the brain coincide with the clusters of activity data, the significance of the clusters of activity may be better understood.

Next, a discriminative mask may be generated to remove activity data that does not have diagnostic value based on their registered location (Step S13). The step of generating the discriminative mask may include applying the generated mask to the data to remove the unwanted information. Then, activation region clustering and filtering may be performed (Step S14) to emphasize clusters of brain activity over isolated activity that may be associated with noise or brain function that is not of diagnostic value. Then, activation region pattern classification may be performed (Step S15) to build classifiers that can be used for characterizing a subsequent patient as either having or not having neuropsychiatric disease. Steps S11 through S15 form a discovery pipeline 10 that may be used to discover the classifiers used to distinguish between a subsequent patient having the neuropsychiatric disease in question and a subsequent patient that does not have the neuropsychiatric disease in question. Each of the steps of FIG. 1 will now be discussed in greater detail.

In Step S11, the functional neuroimaging data is acquired. Acquisition of this data may be accomplished either by performing a brain scan such as an fMRI or by recalling stored image data. The acquired functional neuroimaging data may be activity data indicating regions of brain activity.

Pre-processing and registration of the functional neuroimaging data (Step S12) may be used to better understand what regions of the brain were responsible for exhibiting the acquired activity data. Thus this step may involve mapping the activity data onto an atlas of the brain. As the atlas of the brain may be of a different scale and orientation than the acquired activity data, the activity data may be preprocessed prior to registration so that scale and orientation may match. For example, brain images of an fMRI may be in the form of a 64×64×40 matrix of voxels while the brain atlas data may be in the form of a 45×55×45 matrix. Accordingly, proper scaling and alignment may be performed.

The fMRI data may be acquired in a sequence of images taken over a length of time. For example, the fMRI may be acquired as a sequence of 168 frames over a period of seven minutes. Motion correction may be performed to correct for any movement of the patient during the acquisition of the fMRI sequence. By performing this preprocessing and registration, the activity data may be accurately superimposed over an atlas of the brain so that proper structural context may be given to the activity data. These steps may be preformed automatically with the use of a software package such as an FMRIB Software Library.

Discriminative mask generation (Step S13) may be performed to develop a scheme or mask for the removal of activity data that is of little or no diagnostic value from subsequent neuroimaging data sets. Once created, the discriminative mask may be applied to subsequent data sets to determine from which regions of the brain activity information is valuable so that brain activity information from other regions of the brain may be given less diagnostic value or disregarded. The determination as to which regions of the brain are of diagnostic value may be made by examining a correlation of brain activity for each region of the brain with respect to the experimental group (for example, patients known to have autism) and the control group (for example, patients known to not have autism).

The discriminative mask may contain voxels that demonstrate a difference between the activity of the control group and the experimental group. Those regions that do not show a difference in activity between the groups may be omitted from the discriminative mask.

The determination as to whether to include a given brain region into the discriminative mask may be made in accordance with a predetermined threshold of correlation whereby a region of the brain is added to the discriminative mask when the region exhibits a degree of difference between the control group and the experimental group that is above a predetermined threshold level.

Accordingly, the mask may be used in a positive sense to include regions of the brain that appear to discriminate between patients having the given neuropsychiatric disease, for example, autism, and patients who are free of the neuropsychiatric disease. Then, after clustering, regions of the brain may be found that correlate with the case/control label.

In generating the discriminative mask, the brain may be divided into any number of regions, for example, the brain may be divided into five important regions: (1) cortex, (2) brain stem, (3) cerebellum, (4) thalamus, and (5) lateral ventricles. The discriminative mask may then indicate whether activity data from each brain region should be used or disregarded. As imaging technology improves and understanding of the structure of the brain advances, it may be desirable to divide the brain into a larger number of smaller regions.

Clustering and filtering (Step S14) may involve providing emphasis to activity data that occurs in clusters and remove activity data that is not clustered. This step may be based on the assumption that meaningful brain activity data is highly likely to appear as part of a cluster of activity whereas noise is likely to appear as small isolated instances of activity. Activity data that presents in isolation rather than in a cluster may be disregarded, even if it is found to be in a region of the brain that is not removed by the diagnostic mask. Accordingly, techniques such as mean shifting may be applied to identify and emphasize clusters of activity.

To perform mean shifting, a mean shift algorithm may be applied to the activity data. A mean shift algorithm is a non-parametric clustering technique that does not require the use of prior knowledge of the number of clusters, and does not place a constraint on the shape of the clusters. Based on kernel density estimation theory, the feature space can be regarded as the empirical probability density function (p.d.f.) of the represented parameter. Given n data point $x_i (i=1, \ldots n)$ in the d-dimensional space $R^d$, the multi-variate kernel density estimator with kernel $K(x)$ and a symmetric positive definite d×d bandwidth matrix H may be expressed as:

$$\hat{f}(x) = \frac{1}{n}\sum_{i=1}^{n} K_H(x - x_i) \qquad (1)$$

where:

$$K_H(x-x_i) = |H|^{-1/2} K(H^{-1/2} x) \qquad (2)$$

In practice, the bandwidth matrix may be chosen either as diagonal $H = \text{diag}[h_1^2, \ldots, h_d^2]$, or proportional to the identity matrix $H = h^2 I$. Where the bandwidth matrix is chosen to be proportional to the identity matrix $H = h^2 I$, and the bandwidth parameter $h > 0$, then:

$$\hat{f}(x) = \frac{1}{nh^d}\sum_{i=1}^{n} K_H\left(\frac{x - x_i}{h}\right) \qquad (3)$$

Radically symmetric kernels are a special case that satisfy the following equation:

$$K(x) = c_{k,d} k(\|x\|^2) \qquad (4)$$

where $K(x)$ is the profile of the kernel ($x \geq 0$) and $c_{k,d}$ is the normalized constant that is assumed to be strictly positive. Accordingly, $K(x)$ integrates to 1.

When expressed in profile notation, the density estimator of equation (3) may be rewritten as:

$$\hat{f}(x) = \frac{c_{k,d}}{nh^d} \sum_{i=1}^{n} k\left(\left\|\frac{x-x_i}{h}\right\|^2\right) \qquad (5)$$

The modes of the density may then be found from among the zeros of the gradient ∇f(x)=0. The mean shift may be used to locate the zeros without first estimating the density. By computing ∇f(x) and letting g(x)–k'(x), equation (5) may be expressed as:

$$\hat{\nabla}_{h,K} f(x) = \frac{2c_{k,d}}{nh^{d+2}} \left[\sum_{i=1}^{n} g\left(\left\|\frac{x-x_i}{h}\right\|^2\right)\right] \left[\frac{\sum_{i=1}^{n} x_i g\left(\left\|\frac{x-x_i}{h}\right\|^2\right)}{\sum_{i=1}^{n} g\left(\left\|\frac{x-x_i}{h}\right\|^2\right)} - x\right] \qquad (6)$$

where the second term in equation (6) represents the mean shift, which is the difference between the weighted mean using the kernel G for weight and the center of the kernel x:

$$m_{h,G}(x) = \frac{\sum_{i=1}^{n} x_i g\left(\left\|\frac{x-x_i}{h}\right\|^2\right)}{\sum_{i=1}^{n} g\left(\left\|\frac{x-x_i}{h}\right\|^2\right)} - x \qquad (7)$$

The mean shift vector at location x computed using kernel G is proportional to the normalized density gradient estimate obtained with kernel K. The mean shift vector accordingly points toward the direction of the maximum increase in the density. The mean shift procedure may be performed by repeated computation of the mean shift kernel $m_{h,G}(x)$ and translation of kernel G(x) by $m_{h,G}(x)$. By performing this procedure, convergence will occur at a nearby point where the estimate has zero gradient, where the kernel K has a convex and monotonically decreasing profile.

As discussed above, the mean shift vector points toward the direction of the maximum increase in the density. The mean shift procedure, obtained by repeated computation of the mean shift vector $m_{h,G}(x)$ followed by the translation of the window $x_{t+1} = x_t + m_{h,G}(x_t)$ converges to a point where the gradient of density function is zero. The set of all locations that converge to the same mode defines the basin of attraction of that mode. Then, all points that are determined to be in the same basin of attraction may then be associated with the same cluster.

In step S15, activation region pattern classification may be performed to build classifiers that can be used for characterizing a subsequent patient as either having or not having neuropsychiatric disease. Here, classifiers may be established from the acquired image data that are here used as training data, for separating the activity data of healthy patients from those patients with neuropsychiatric disease. These classifiers, once established, may then be used on a case-by-case basis to differentiate between healthy patients and patients with neuropsychiatric disease.

Any known approach may be used to generate these classifiers, however, exemplary embodiments of the present invention may utilize Principal Component Analysis (PCA) and/or Linear Descriptive Analysis (LDA) to generate the classifiers.

Principal Component Analysis (PCA), is a statistical technique for reducing multidimensional datasets to lower dimensions to simplify the analysis used to generate the appropriate classifiers. PCA uses linear transformation that transforms the data to a new coordinate system so that the greatest variance by any projection of the data comes to lie within the first coordinate, the second greatest variance lies on the second coordinate, and so on. PCA may be used to reduce the dimensionality of the dataset while retaining those characteristics of the dataset that contribute most to its variance, by keeping lower-order principal components and ignoring higher-order components.

For a data matrix with a zero empirical mean X (the empirical mean of distribution has been subtracted from the dataset), where each column represent a different repetition of the fMRI imaging, and each row gives the result from a particular voxel in the image, the PCA transformation may be expressed as:

$$Y = W X = \Sigma V^T \qquad (8)$$

where WΣV$^T$ is the singular value decomposition (svd) of X.

Then, the reduced-space data matrix may be obtained by projecting X down to the reduced space using only the first L singular vectors, $W_L$:

$$Y = W_L^T X = \Sigma_L V_L^T \qquad (9)$$

While PCA may be used to find principal components to maximize the variance of the data, linear discriminative analysis (LDA) may be used to find the most discriminative dimensions of the data among classes. LDA may be used in statistics to find the linear combination of features which best separate two or more classes of object or event.

The initial fMRI data may be characterized by a set of training data observations x made up of scans of patients known to either have or be free of neuropsychiatric disease. The classification problem is then to find a good predictor for the class y of any given sample of the same distribution given the observations x. LDA approaches this problem by assuming that the probability of an input x being in a class y is purely a function of the following combination of the known observations:

$$S = \frac{\sigma_{between}^2}{\sigma_{within}^2} = \frac{(\vec{w} \cdot \vec{\mu}_{y=1} - \vec{w} \cdot \vec{\mu}_{y=0})^2}{\vec{w}^T \sum_{y=1} \vec{w} + \vec{w}^T \sum_{y=0} \vec{w}} \qquad (10)$$

Accordingly, the maximum separation occurs when:

$$\vec{w} = (\Sigma_{y=1} + \Sigma_{y=0})^{-1} (\vec{\mu}_{y=1} - \vec{\mu}_{y=0}) \qquad (11)$$

In generating the classifiers from the training data, leave one out cross validation (LOOCV) and/or receiver operating characteristic (ROC) curves may be used to verify the accuracy of the generated classifiers (Step S16). If the result of this verification is inconclusive or suggests that the generated classifiers may not be accurate (No, Step S16), then the discovery pipeline 10 (Steps S11 through S15) may be repeated with additional training data until the accuracy of the generated classifiers can be successfully validated (Yes, Step S16) and the generated classifiers can be accepted (Step S17).

Leave one out cross validation (LOOCV) and Receiver Operating Characteristic (ROC) curves may be used to verify whether the classifiers have been effectively generated. Leave-one-out cross-validation (LOOCV) involves using a single observation removed from the training data as the validation data. Thus a particular instance of training data, for example, representing one patient, may be removed from the set of training data. Then the classifiers may be generated without this particular instance of data. Finally, after the classifiers have been generated, they may be tested upon the particular instance of data to see if the classifiers can effectively classify the left-out instance of data in accordance with its known disposition.

Figure 2:
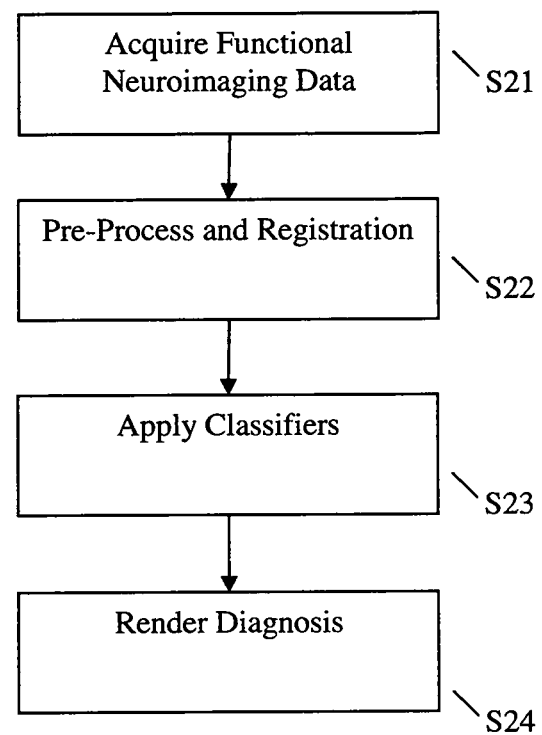
FIG. 2 is a flow chart illustrating a diagnostic pipeline for identification of neuropsychiatric disease according to an exemplary embodiment of the present invention.

As discussed above, Steps S11 through S15 form a discovery pipeline 10 that may be used to discover the classifiers used to distinguish between a subsequent patient having the neuropsychiatric disease in question and a subsequent patient that does not have the neuropsychiatric disease in question. However, after the discovery pipeline has resulted in the creation of suitable classifiers, a diagnostic pipeline may be followed to utilize the discovered classifiers for the identification of neuropsychiatric disease. FIG. 2 is a flow chart illustrating a diagnostic pipeline for identification of neuropsychiatric disease according to an exemplary embodiment of the present invention.

First, functional neuroimaging data is acquired for a subsequent patient (the subsequent patient is a patient for whom functional neuroimaging data has been acquired after the creation of classifiers) (Step S21). This functional neuroimaging data is different than the functional neuroimaging data that was acquired during the creation of the classifiers, the latter of which is considered training data. Acquisition of this data may be accomplished either by performing a brain scan such as an fMRI or by recalling stored image data. The acquired functional neuroimaging data may be activity data indicating regions of brain activity.

Next, the functional neuroimaging data may undergo pre-processing and/or registration (Step S22). Preprocessing and registration may be, for example, as described above with reference to FIG. 1. Then, one or more of the generated classifiers may then be applied to the pre-processed functional neuroimaging data (Step S23) and it may be determined whether the subsequent patient has or does not have the neuropsychiatric disease in question, for example, autism (Step S24). This step (Step S24) may be a rendering of a diagnosis and may be performed automatically based on the results of the application of the one or more classifiers, or may be performed by a medical practitioner such as a radiologist or neurologist based, at least in part, in the results of the application of the one or more classifiers.

Accordingly, exemplary embodiments of the present invention may be used to determine which regions of the brain may correspond to a particular neuropsychiatric disease, generate one or more classifiers for the particular neuropsychiatric disease, and/or to determine whether a particular patient has or does not have the particular neuropsychiatric disease.

Exemplary embodiments of the present invention are not limited to the generation of classifiers as discussed above with respect to FIG. 1 and/or the diagnosis of disease based on the classifiers as discussed above with respect to FIG. 2. Exemplary embodiments of the present invention may be utilized for the purposes of determining one or more regions of the brain that may be involved in a particular neuropsychiatric disease. By identifying these involved regions, scientific research may be directed to these areas with the goal of better understanding the nature of the particular neuropsychiatric disease, a step that may advance the pursuit of an effective treatment or cure. When it is desired that involved regions be discovered, Steps S11 through S14 (discussed above with respect to FIG. 1) may be performed, with the ultimate result being clusters of significant activation regions superimposed or otherwise associated with particular regions of the brain. Thus because of the effective processing and filtering steps described in detail above, the regions of the brain associated with the significant activation regions may be identified as "involved regions." The resulting involved regions may then be the focus of further research.

Figure 3:
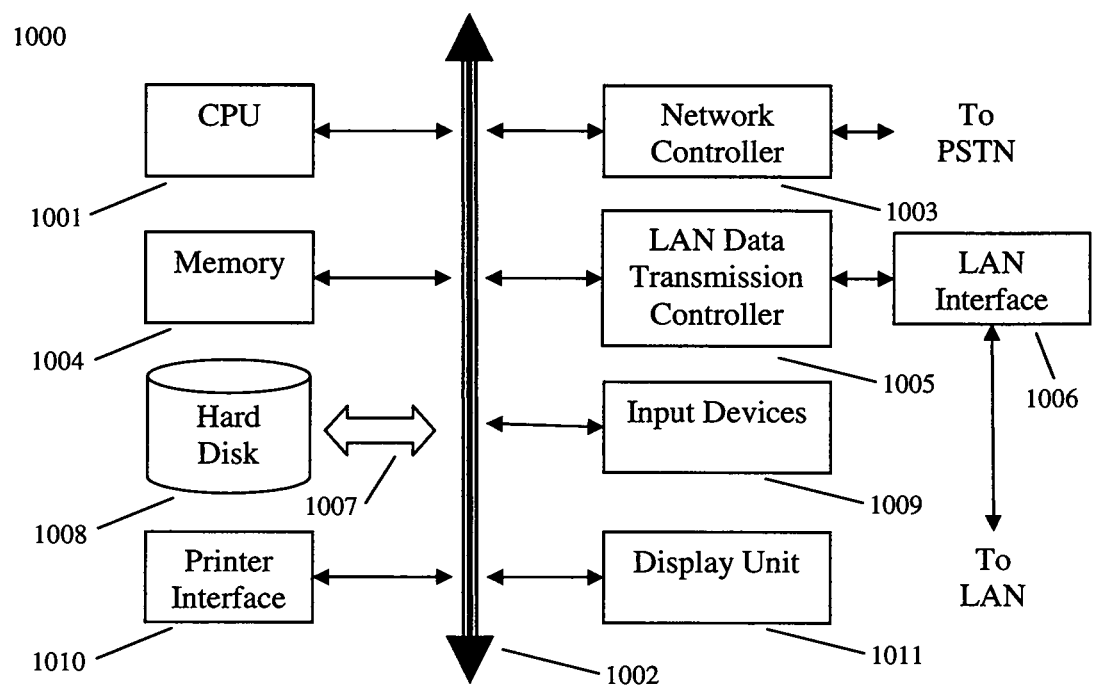
FIG. 3 shows an example of a computer system capable of implementing the method and apparatus according to embodiments of the present disclosure.

FIG. 3 shows an example of a computer system which may implement a method and system of the present disclosure. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

The computer system referred to generally as system 1000 may include, for example, a central processing unit (CPU) 1001, random access memory (RAM) 1004, a printer interface 1010, a display unit 1011, a local area network (LAN) data transmission controller 1005, a LAN interface 1006, a network controller 1003, an internal bus 1002, and one or more input devices 1009, for example, a keyboard, mouse etc. As shown, the system 1000 may be connected to a data storage device, for example, a hard disk, 1008 via a link 1007.

Exemplary embodiments described herein are illustrative, and many variations can be introduced without departing from the spirit of the disclosure or from the scope of the appended claims. For example, elements and/or features of different exemplary embodiments may be combined with each other and/or substituted for each other within the scope of this disclosure and appended claims.

What is claimed is:

1. A method for identifying neuropsychiatric disease, comprising:
   acquiring functional neuroimaging data of a patient; and
   applying a classifier for identifying the neuropsychiatric disease to the acquired functional neuroimaging data to determine whether the patient has the neuropsychiatric disease, wherein the classifier is generated by:
   acquiring functional neuroimaging training data of patients known to have the neuropsychiatric disease and patients known not to have the neuropsychiatric disease;
   registering the acquired functional neuroimaging training data to an atlas of the brain;
   generating a discriminative mask based on the registered functional neuroimaging training data;
   applying the generated discriminative mask to the registered functional neuroimaging training data to remove unwanted information;
   differentiating between clusters of neural activity and isolated regions of neural activity from within the masked functional neuroimaging training data;
   emphasizing the clusters of neural activity over the isolated regions of neural activity; and
   generating the classifier for identifying neuropsychiatric disease based on the cluster-emphasized functional neuroimaging training data.

2. The method of claim 1, wherein prior to registering the acquired functional neuroimaging training data to an atlas of the brain, the acquired functional neuroimaging training data is pre-processed to place the acquired functional neuroimaging data into a scale and orientation that matches the atlas of the brain and to correct for patient motion during the acquiring functional neuroimaging training data.

3. The method of claim 1, wherein generating the discriminative mask based on the registered functional neuroimaging training data includes examining a correlation of brain activity for each region of the brain with respect to functional neuroimaging training data from the patients known to have the neuropsychiatric disease (an experimental group) and functional neuroimaging training data from the patients known to not have the neuropsychiatric disease (a control group).

4. The method of claim 3, wherein the discriminative mask contains voxels that demonstrate a difference between the activity of the control group and the experimental group and those regions that do not show a difference in activity between the groups are omitted from the discriminative mask.

5. The method of claim 1, wherein differentiating between clusters of neural activity and isolated neural activity and emphasizing the clusters of neural activity over the isolated neural activity includes performing mean shifting to identify and emphasize clusters of activity.

6. The method of claim 1, wherein generating one or more classifiers for identifying neuropsychiatric disease includes performing Principal Component Analysis (PCA) or performing Linear Descriptive Analysis (LDA) to generate the classifiers.

\* \* \* \* \*